(12) United States Patent
Flamm et al.

(10) Patent No.: US 10,497,119 B2
(45) Date of Patent: Dec. 3, 2019

(54) SYSTEM AND METHODS FOR POST-CARDIAC MRI IMAGES

(71) Applicant: Precision Image Analysis, Inc., Kirkland, WA (US)

(72) Inventors: Scott Flamm, Shaker Heights, OH (US); Daniel McInally, Seattle, WA (US); Mary Waiss, Kirkland, WA (US); Philip Trinh, Seattle, WA (US); Sam Alkek, Bellevue, WA (US)

(73) Assignee: Precision Image Analysis, Inc., Kirkland, WA (US)

( * ) Notice: Subject to any disclaimer, the term of this patent is extended or adjusted under 35 U.S.C. 154(b) by 82 days.

(21) Appl. No.: 15/602,075

(22) Filed: May 22, 2017

(65) Prior Publication Data

US 2018/0108132 A1    Apr. 19, 2018

Related U.S. Application Data

(60) Provisional application No. 62/339,652, filed on May 20, 2016.

(51) Int. Cl.
| | |
|---|---|
| *G06K 9/00* | (2006.01) |
| *G06T 7/00* | (2017.01) |
| *G16H 30/40* | (2018.01) |
| *G06T 7/11* | (2017.01) |
| *G06K 9/62* | (2006.01) |
| *G06T 7/12* | (2017.01) |
| *G16H 50/70* | (2018.01) |

(Continued)

(52) U.S. Cl.
CPC ........ *G06T 7/0016* (2013.01); *G06K 9/00201* (2013.01); *G06K 9/6215* (2013.01); *G06K 9/6269* (2013.01); *G06T 7/11* (2017.01); *G06T 7/12* (2017.01); *G16H 30/40* (2018.01); *G16H 50/70* (2018.01); *G06K 2209/051* (2013.01); *G06N 7/005* (2013.01); *G06N 20/00* (2019.01); *G06T 2207/10088* (2013.01); *G06T 2207/30048* (2013.01); *G06T 2219/2021* (2013.01); *G16H 70/60* (2018.01)

(58) Field of Classification Search
None
See application file for complete search history.

(56) References Cited

U.S. PATENT DOCUMENTS

| | | | | |
|---|---|---|---|---|
| 2003/0187358 | A1* | 10/2003 | Okerlund | A61B 6/503 600/443 |
| 2011/0243401 | A1* | 10/2011 | Zabair | G06K 9/00 382/128 |

(Continued)

OTHER PUBLICATIONS

Thomas Chee Tat Ho et al. (An "Approach to Reconstruct Lost Cardiac Signals Using Pattern Matching and Neural Networks via Related Cardiac Information", IEEE, 2010, pp. 441-444) (Year: 2010).*

*Primary Examiner* — Wei Wen Yang
(74) *Attorney, Agent, or Firm* — Newman Du Wors LLP

(57) ABSTRACT

Systems and methods for post processing cardiac magnetic resonance images are described that utilize a machine-learning algorithm. Embodiments of the systems and methods maximize physician and technologist efficiency by minimizing the necessary manual labor that is required to post-process medical images through smart-automation, thereby improving consistency and reproducibility of post-processing results by minimizing operator bias.

11 Claims, 3 Drawing Sheets

(51) Int. Cl.
*G16H 70/60* (2018.01)
*G06N 20/00* (2019.01)
*G06N 7/00* (2006.01)

(56) References Cited

U.S. PATENT DOCUMENTS

2013/0190592 A1* 7/2013 Coppini .................. A61B 5/02
                                                                          600/407
2017/0109881 A1* 4/2017 Avendi ................. G06T 7/0012

* cited by examiner

SYSTEM AND METHODS FOR POST-CARDIAC MRI IMAGES

CROSS REFERENCE TO RELATED APPLICATION

This application claims the benefit of U.S. Provisional Application No. 62/339,652, filed May 20, 2016.

BACKGROUND

Quantitative cardiac results for ventricular function is crucial information and plays a major role in therapeutic decision making, monitoring disease progression, and is of high value concerning diagnostic and prognostic evaluations. However, post-processing medical images to obtain this actionable data is a time-consuming, costly, and laboriously repetitive process despite available semi-automated border detection tools. The current standard practice of manually producing the contours for functional cardiac magnetic resonance imaging (MRI) cases takes approximately 40 minutes and involves manually delineating specific regions of cardiac anatomy leading to inherent high observer-dependent variability. The issue is further perpetuated by advanced analyses such as Feature Tracking or Time-Volume curve quantification which may require hundreds of images to be contoured, unnecessarily requiring a significant amount of dedicated physician or technologist time.

BRIEF SUMMARY

Embodiments of the invention includes systems and methods for post processing cardiac magnetic resonance images (MRIs) to directly alleviate this burden by producing a machine-learning algorithm specifically for performing accurate cardiac post-processing analyses in order to boost physician efficiency, reproducibility, and accuracy. The end-result will allow physicians to save time to focus more directly on patient care and performing specialized tasks at the top-of-their-license.

Embodiments of the invention maximize physician and technologist efficiency by minimizing the necessary manual labor that is required to post-process medical images through smart-automation. Embodiments of the invention will improve consistency, and reproducibility of post-processing results by minimizing operator bias.

Benefits and advantages offered by certain embodiments of the invention in include one or more of the following: (1) reduced costs for image analysis, potentially resulting in a 40% reduction in cost for an average center performing 1500 cardiac MRI's/year, (2) reduced physician time for image analysis, potentially freeing up an average of one hour of physician time per image, which can generate an average $750.00/hour, (3) increased MRI throughput by potentially 1.5-2.0× by reducing or eliminating backlog of unanalyzed studies, (4) increased patient satisfaction by potentially decreasing time to diagnose and treat medical issues using the images, and (5) potential improvements in consistency and reliability of results from image analysis.

DETAILED DESCRIPTION

Figure 1:
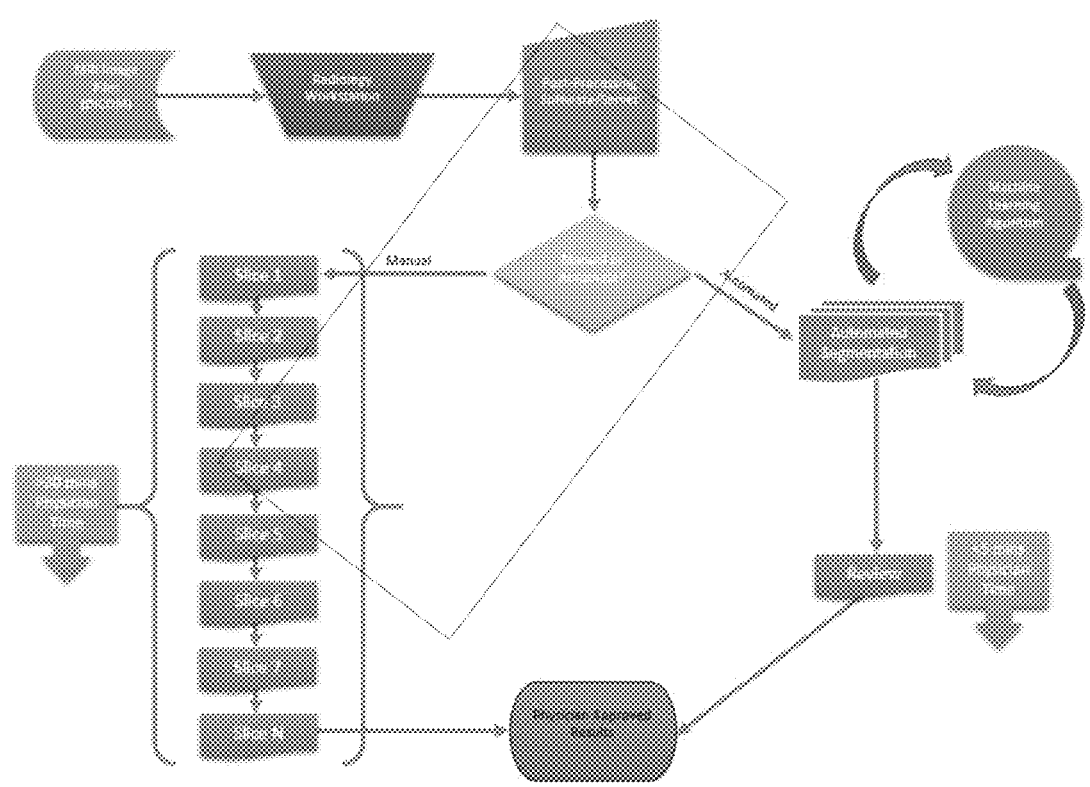
FIG. 1 is the general process for the post-processing of cardiac magnetic resonance imaging (MM) images. The dotted line box surrounds the portion that this invention processes.

Embodiments of the present invention include a stand-alone system and method supported by a machine learning framework compatible with traditional post-processing workstations, ensuring maximum benefit in both the clinical and research cardiac imaging environments. In embodiments, no additional hardware is required, enabling the system and method to supplement or replace current solutions to empower and advance cardiac imaging post-processing analyses.

In embodiments, the proposed system and method uses a machine learning algorithm to provide operators with a more efficient, highly reproducible, and automated alternative to manually contouring and segmenting cardiac medical images. Using a machine learning algorithm that stores segmentation data in real-time also allows future follow-up visits from the patient to be completed at ever increasing efficiency as the program is designed to and can incorporate and tag the patient's prior three-dimensional (3D) cardiac structure into memory, so only minor revisions on the follow-up exam will be necessary. Furthermore, the reviewing and editing habits of physicians can be tracked so repetitive corrections could be a reduced or even eliminated.

Embodiments of the invention will store an ever-evolving library of pre-contoured and established cardiac structures, providing a baseline knowledge of cardiac shapes. In embodiments, this library of reference will evolve with each new case that is analyzed and finalized by the physician—enabling the system to learn and expand its knowledge with each and every interaction. If the physician specializes in complex congenital heart disease and contours these types of cases on a regular-basis for example, the algorithm will store each finalized case and "learn" with each newly added heart. The more cases that are contoured, the better the algorithm becomes. Follow-up visits from the patient will be completed at increasing efficiency, as the program incorporated the patient's 3D cardiac structure into its memory banks from the previous exams, so only minor edits will be necessary.

Z-score restrictions can be enforced on the program—allowing it to only contour and morph structures within proven geometric restrictions of anatomically correct shape boundaries to a certain quantitative well-defined limit. If a particular heart's morphology falls outside of these set limitations, the physician can still make manual edits over-riding the automated segmentation through manual edits with newfound knowledge knowing that:

a. The analyzed heart's 3D shape may be of a particular interest as it falls outside of the typical/normal range seen by the program's library.
b. The exact anatomical location of where these shape peculiarities lie.
c. The quantitative and qualitative correlation and/or deviations from a typical reference heart, ie: the amount of manual corrections necessary and the change in volume from normal/typical hearts found in the library.

Embodiments of the system and method in accordance with the invention will be described with reference to FIGS. 1 through 6.

FIG. 1 depicts the general process for the post-processing of cardiac MRI images. Embodiments of this invention can replace the manual post-processing of these images. The dotted line rectangle in the figure indicated the portion of the general process that can be processed by an embodiment of this invention.

Figure 2:
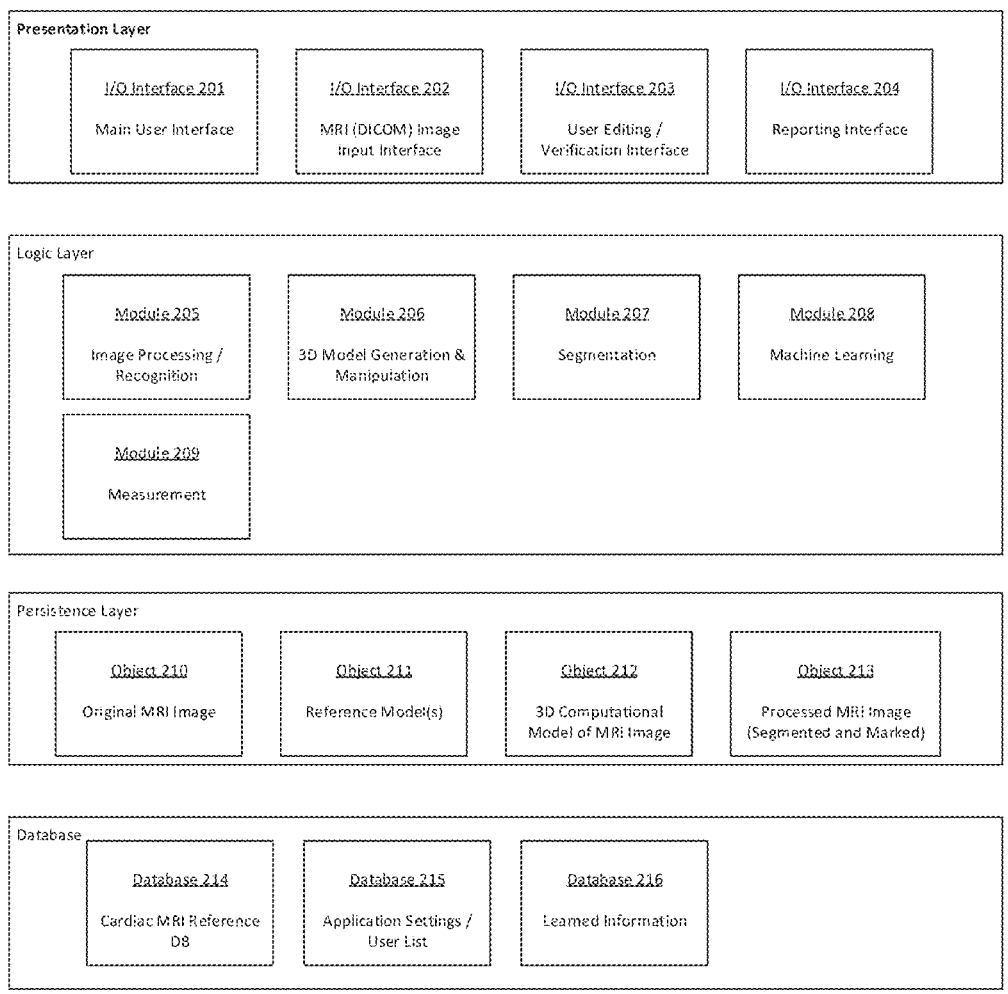
FIG. 2 is the software architecture and components for an application for post-processing cardiac MRI images.

FIG. 2 depicts the software architectural components of an embodiment of this invention. The software will be developed in one or more languages with the necessary math functions, such as Python and C#.NET programming languages.

With reference to FIG. 2, the presentation layer show the four primary input/output interface according to an embodiment of the invention. I/O Interface 201 is the primary user interface, where the user can input program setting, and initiate a post-process to occur. I/O Interface 202 is the raw MRI image input interface, where the original image file location is selected and imported. I/O interface 203 is the user image editing and verification interface. Here the original image and the generated 3D model can be visually compared by the user and the user can make adjustments to the 3D model. When the end user determines the 3D model is acceptable can then select an approval bottom or alternatively approval +add to reference database. I/O Interface 204 is the reporting interface where the user can select options and customer formatting for the outputted report.

With reference to FIG. 2, the logic layer show the five primary software module according to an embodiment of the invention. Module 205 contains all the image processing and image recognition/matching routines. These routines include image matching by using histogram matching, Discrete Fourier Transform matching and hash creation and matching. These methods will be used for both 3D model matching and slice edge detection. Module 206 contains the 3D model generation and manipulation routines. The structure of image objects will be in the form of m×n matrices and routines on module 206 will perform all the basic matrix translation, rotation, and scaling operations. It also performs matrix duplication. Module 207 perform segmentation of the MRI image. Using known industry standard for segmentation and user input routines in Module 207 will determine the slice planes that can be used for slicing the computational model as well as the original MRI image. Module 208 contains the machine learning routines that will be used in several areas of this embodiment of the invention. Semi-Supervised learning will be used in the image matching routine learn from correct and incorrect matches. K-nearest neighbors and/or Bayesian classifier algorithms will be used in both the matching of the full 3D object as well as the edge detection routines used to improve the accuracy of the cardiac membrane edges in the 2D slices of the MRI image. Module 209 perform the measurement calculations on the computational image 212 that is desired by the user and will be outputted in a detailed report.

With reference to FIG. 2, the persistence layer shows the four primary objects according to an embodiment of the invention. These persistence objects are store in memory of the running application and will use matrices to store image data. Object 210 is the imported Original MRI Image. Object 211 is one or more Reference Model loaded from the Reference DB 214. Object 212 is the 3D Computational Model that is first copied from the best match reference model and then adjusted to be a high accuracy model of the original MRI to be used for calculations and measurements. Object 213 is a modified copy of the Original MRI Image.

With reference to FIG. 2, the database layer shows the three primary database according to an embodiment of the invention. Database 214 is the Cardiac MRI Reference Database that stores 3D models of known and verified post-processed cardiac MRI Images. These are used to match with the imported Original MRI Image 210 to determine the cardiac structure and for use as a baseline computational model. After image matching is conducted and after a final post-processed MRI image is verified as being correct additional MRI images are added to this database to improve the system's ability to detect structures and create usable computational models. Database 215 is the application settings and user list database that stores the applications basic configuration setting, security setting, and user access control list and well as application log information for troubleshooting. Database 216 is the Learned Information Database and contains tables of learned information that is stored by Machine Learning Module 208. Some of the important machine learning tables stored is statistical information from the pattern matching routines the record fastest image matching method, reference images most used and most performed matrix manipulations. These are used by the Machine Learning Module 208 to better predict the best process when encountering new Original MRI Images 210.

Figure 3:
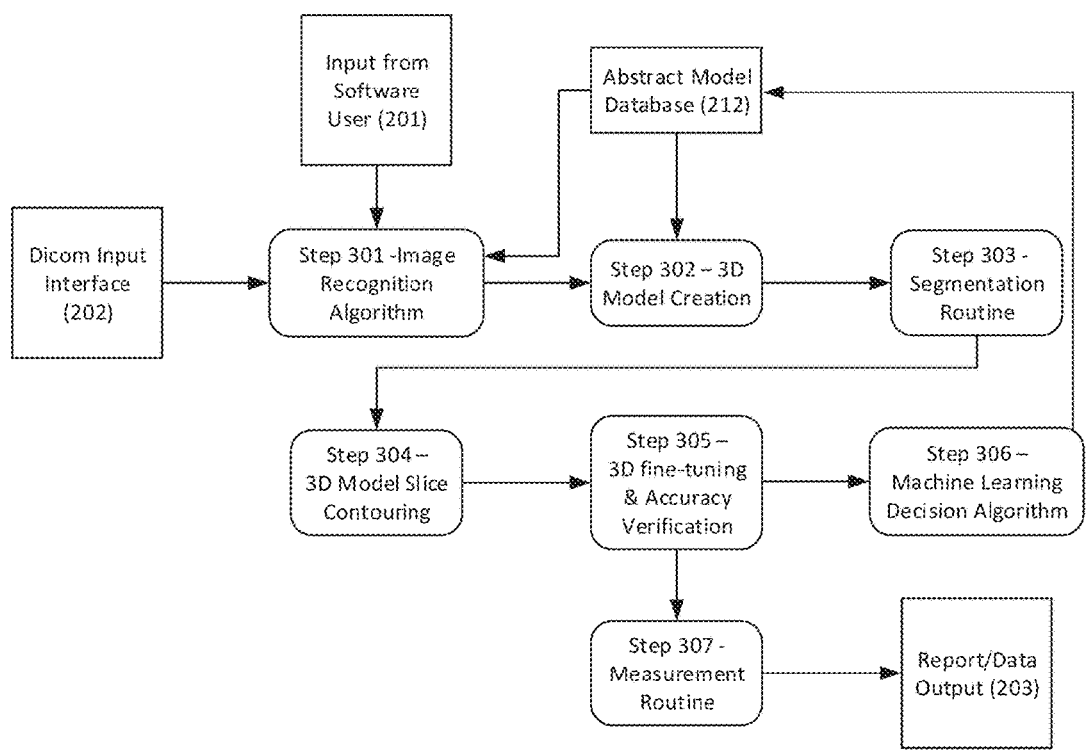
FIG. 3 is a flowchart showing a method for post-processing cardiac images according to an embodiment of the invention.

FIG. 3 depicts a flowchart showing a method for post-processing cardiac images according to an embodiment of the invention. The embodiment includes the key steps in an image recognition, segmentation and measurement process, which serves as an alternate image post-processing workflow incorporating automatic border segmentation utilizing Machine Learning Algorithms.

With reference to FIG. 3, at Step 301, the DICOM Input Interface 202 imports cardiac medical images from raw format either directly from a hard file or from a PAX system into a persistent object (Object 210). This object with be an m×n matrix that holds the pixel information of the original MRI Image. During the import, a routine (in Module 205) performs initial validation of the data set and prepared images for Image Recognition routine. This preparation includes checking and verifying the reference axis (slice position) and image integrity (any loss of pixels by percentage as a rejection criteria).

With reference to FIG. 3, at Step 301, Image Recognition Algorithm (module 205) receives the Original MRI image object (210) from the DICOM Input Interface 202. Image Recognition Algorithm 205 uses input from the User 201 and data from an Abstract Model Reference Database 214 to quickly identify cardiac structures that are either selected by the User 201 or is auto recognized by pattern matching. Abstract models from the Abstract Model Database (214) are represented as m×n matrices (Object 211) and are compared to the Original (210). Fouler transform, histogram, and hash matching as well as several other pattern matching methods will be used to extract features (by edge detection, grey level thresh holing, etc.) and match the Original 210 to a reference Image 211. Also, machine learning routines from the Machine Learning Module 208 will use semi-supervised machine learning classification algorithm (Including Bayesian, k-Nearest Neighbor, and Dimensionality Reduction). Particularly a reduced dimension characterization feature set will be generated and used in addition to direct image pattern matching to improve performance by more quickly creating a pattern match with fewer computational operations. The system with auto adjust to different methods as needed to complete a high accuracy pattern match in the shortest time.

As for input by a User (Interface 201), the algorithm may require either an initial selection of cardiac structure to analyze, a few anatomical markings or characteristics (Such as length of left ventricle). Once the cardiac structure is quickly and loosely located—the program will interpolate and extrapolate the appropriate 3D structure filling in all the necessary information on the short-axis cardiac images (if applicable) and producing a 3D shape that can be reviewed and edited in the source images series as necessary.

With reference to FIG. 3, at Step 302, a 3D Computational Model 212 is generated by the 3D Model Generation module 206. The 3D Computational Model 212 is generated from making a duplicate m×n matrix of the matching model from the abstract model reference database and then using transformations, rotations, scaling is modified to a high accuracy match of the original raw medical image 210.

With reference to FIG. 3, at Step 303, Segmentation Module 207 determines the appropriate number of slices needed basic in type and size of cardiac structure and known standards and then creates slices trajectories of both the Raw DICOM image 210 and the computational model 212. These slices will be used refine the feature and edge accuracy of the computational model 212. The computational model can then be used to mark the structures and segment the original image and produce the Processed MRI image 213. The determine segmentation slices will be stored with the image data in Object 213.

With reference to FIG. 3, at Step 304, 3D Model Slice Contouring is performed from routines in image processing using module 205 and module 206 by using standard image recognition techniques such as edge detection or gray level thresholding at each slice to make corrections to the 3D Computational Model 212. Machine learning can also be used to improve the contouring process the by error measurement and a basic regression routine from module 208.

With reference to FIG. 3, at Step 305, 3D Fine Tuning & Accuracy Verification is performed using routines from Image Recognition 206 and 3D Manipulation 206 to improve the accuracy of the 3D Computational Model 211 to a level that is acceptable by medical radiological standards. Using the User Editing and Verification Interface 203, User 201 can review and make corrections to the 3D Computational Model 212 as needed by comparing with the Original MRI Image 210 and select options for model inclusion in the abstract image reference database 214. The image reference database 214 will be a standard open sources or free relational database (like SQL Server express or mysql). Image matrix data and other associated data will be store in tables with primary identifiers.

With reference to FIG. 3, at Step 306, routines in the Machine Learning module 208 performs semi-supervised machine learning techniques to incorporate the 3D Computational Model 212 and other characteristics of each analyzed cardiac image into the database of reference abstract models. Initially the incorporation of a new reference MRI model will be by user choice but a system of automatic error calculation and image incorporation will be designed that used measured errors from the image matching and contouring that will auto populate the reference image database 214. Standard default reference databases can be produced to best fit the most popular industry standards such as: ACCF/SCCT/ACR/AHA/ASE/ASNC/NASCI/SCAI/SCMR to enable industry established or custom segmentation protocols that enable: 1) Exclusion of the trabeculations and papillary muscles from the blood pool, 2) Inclusion of the trabeculations and papillary muscles into the blood pool, 3) Exclusion of the outflow tracts, and/or 4) Atrial exclusion segmentation.

With reference to FIG. 3, at Step 308, a Measurement Routine (module 209) takes the refined 3D Computational Model 212 and performs the needed CMR post-processing calculations and measurements as selected by the software user (such as volumes and lengths of cardiac structures, value size, etc.). A report will be generated that contains the results of the measurements as selected by end user. This report will be in one or more format that are defined by end user (MS Word, PDF, DICOM, etc.). The final processed MRI image, Object 213, will be an augmented matrix adding segmentation and measurement data to the original MRI image data.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method for post-processing cardiac MRI images, the method comprising:
   importing first cardiac image data into a first matrix;
   performing an initial validation of the first cardiac image data;
   evaluating the first cardiac image data and identifying cardiac structures using pattern matching against a database of known cardiac structures;
   extrapolating 3D cardiac structure between the identified cardiac structures;
   producing a 3D cardiac shape combining data from the extrapolated 3D cardiac structures and data from the identified cardiac structures;
   generating a 3D model of the 3D cardiac shape by creating a second matrix of data of the 3D cardiac shape;
   comparing the 3D cardiac shape data to the first cardiac image data;
   segmenting the 3D model of the 3D cardiac shape and the first cardiac image data;
   contouring the 3D model of the 3D cardiac shape using the segments of the 3D model of the 3D cardiac shape and the first cardiac image data;
   verifying the 3D model of the 3D cardiac shape using image recognition and user input; and
   incorporating the verified 3D model of the 3D cardiac shape into the database of known cardiac structures.

2. The method of claim 1, wherein the pattern matching utilizes a semi-supervised machine learning classification algorithm.

3. The method of claim 2, wherein the semi-supervised machine learning classification algorithm utilizes input from a user identifying cardiac areas to analyze.

4. The method of claim 1, further comprising performing CMR post-processing of the verified 3D model of the 3D cardiac shape.

5. The method of claim 4, further comprising generating a report containing the measurements from the CMR post-processing of the verified 3D model of the 3D cardiac shape.

6. A non-transitory machine readable storage medium having stored thereon a computer program capable of perming the method of claim 1.

7. A system for post-processing cardiac magnetic resonance imaging (MRI) images, the system comprising:
- an input interface where cardiac images are imported into the system;
- a database where data representing the imported cardiac images are stored in a matrix;
- a second input interface where a user can mark regions of interest on the cardiac images;
- an image recognition module that identifies cardiac structures from the data representing the imported cardiac images, including from evaluation of the marked regions of interest;
- a three dimensional (3D) model generator that generates a 3D model of the cardiac structures identified by the image recognition module;
- a segmentation module that segments the 3D model of the cardiac structures into slices;
- a three dimensional (3D) slice contouring module that performs image recognition and image corrections to the segmented slices from the segmentation module;
- a three dimensional (3D) fine tuning and accuracy verification module that performs image recognition and 3D manipulation to improve the accuracy of the 3D model of the cardiac structures; and
- a post-processing module that performs pre-selected calculations and measurements on the 3D model from the three dimensional (3D) fine tuning and accuracy verification module.

8. The system of claim 7, wherein the image recognition module that identifies cardiac structures compares the data representing the imported cardiac images to a database of known cardiac structures.

9. The system of claim 7, wherein the three dimensional (3D) fine tuning and accuracy verification module utilizes a semi-supervised machine learning classification algorithm.

10. The system of claim 7, wherein the post-processing module is configured to perform CMR post-processing and is further configured to generate a report containing the measurements from the CMR post-processing.

11. An apparatus for post-processing cardiac magnetic resonance imaging (MRI) images, the apparatus comprising:
- a DICOM an input interface configured to import cardiac MRI image data;
- a database configured to store the cardiac MRI image data;
- a second input interface configured to permit a user to mark regions of interest in the cardiac MRI image data;
- an image recognition module configured to identify known cardiac structures in the marked cardiac MRI image data;
- a 3D generator configured to create a 3D model of the cardiac MRI image data;
- a segmentation module configured to segment the 3D model into MRI slices;
- a 3D slice contouring module configured to recognize known structures in the MRI slices and make corrections to the MRI slices;
- a 3D fine tuning and accuracy verification module configured to recognize structures in the 3D model and manipulate the 3D model to improve its accuracy;
- a post-processing module configured to perform user selected calculations and measurements on the 3D model; and
- a report generator configured to generate a report containing the user selected calculations and measurements on the 3D model.

\* \* \* \* \*